United States Patent [19]

Nelson

[11] 4,088,694

[45] May 9, 1978

[54] 2-DECARBOXY-2-HYDROXYMETHYL-11-DEOXY-PGE$_2$ ANALOGS

[75] Inventor: Norman A. Nelson, Galesburg, Mich.

[73] Assignee: The Upjohn Company, Kalamazoo, Mich.

[21] Appl. No.: 786,152

[22] Filed: Apr. 6, 1977

Related U.S. Application Data

[62] Division of Ser. No. 647,369, Jan. 8, 1976, Pat. No. 4,032,576.

[51] Int. Cl.$^2$ .................... C07C 49/46; C07C 49/80; C07C 49/82
[52] U.S. Cl. ............................................... 260/586 R
[58] Field of Search ................................ 260/586 R

[56] References Cited

PUBLICATIONS

Derwent Farmdoc CPI 76109U-B (German Offenlegungsschrift, No. 2,323,127, 09-05-72).

Primary Examiner—Gerald A. Schwartz
Attorney, Agent, or Firm—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

15 Claims, No Drawings

2-DECARBOXY-2-HYDROXYMETHYL-11-DEOXY-PGE₂ ANALOGS

The present application is a divisional application of Ser. No. 647,369 filed Jan. 8, 1976, now issued as U.S. Pat. No. 4,032,576 on June 28, 1977.

The present invention relates to prostaglandin analogs, for which the essential material constituting disclosure therefor is incorporated by reference here from Ser. No. 647,369, filed Jan. 8, 1976, now U.S. Pat. No. 4,032,576.

I claim:

1. A prostaglandin analog of the formula

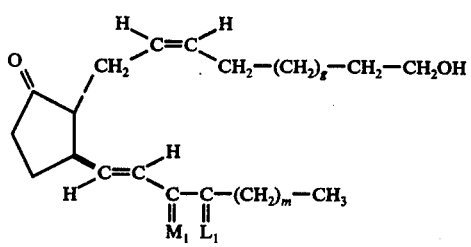

wherein $M_1$ is

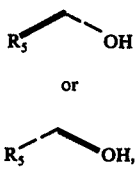

or

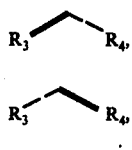

wherein $R_5$ is hydrogen or methyl;
wherein $L_1$ is

or a mixture of

and wherein $R_3$ and $R_4$ are hydrogen, methyl or fluoro, being the same or different, with the proviso that one of $R_3$ and $R_4$ is methyl only when the other is hydrogen or methyl;

wherein $g$ is one, 2, or 3; and
wherein $m$ is one to 5, inclusive;
with the proviso that at least one of $R_3$, $R_4$, and $R_5$ is methyl or at least one of $R_3$ and $R_4$ is fluoro.

2. A compound according to claim 1, wherein $m$ is one or 2.

3. A compound according to claim 1, wherein $m$ is 4 or 5.

4. A compound according to claim 1, wherein $m$ is 3.

5. A compound according to claim 4, wherein $g$ is one.

6. A compound according to claim 5, wherein at least one of $R_3$ and $R_4$ is fluoro.

7. A compound according to claim 6, wherein $R_3$ and $R_4$ are both fluoro.

8. A compound according to claim 7, wherein $R_5$ is hydrogen.

9. 2-Decarboxy-2-hydroxymethyl-16,16-difluoro-11-deoxy-PGE₂, a compound according to claim 8.

10. A compound according to claim 5, wherein at least one of $R_3$ and $R_4$ is methyl.

11. A compound according to claim 10, wherein $R_3$ and $R_4$ are both methyl.

12. A compound according to claim 11, wherein $R_5$ is hydrogen.

13. 2-Decarboxy-2-hydroxymethyl-16,16-dimethyl-11-deoxy-PGE₂, a compound according to claim 12.

14. A compound according to claim 5, wherein $R_3$ and $R_4$ are hydrogen and $R_5$ is methyl.

15. 2-Decarboxy-2-hydroxymethyl-15-methyl-11-deoxy-PGE₂, a compound according to claim 14.

* * * * *